United States Patent [19]

Besecker et al.

[11] Patent Number: 4,990,638

[45] Date of Patent: Feb. 5, 1991

[54] WATER-SOLUBLE ANTIMONY (V) COMPOUNDS

[75] Inventors: Charles J. Besecker, Cleveland; William A. Marritt, Cleveland Hts., both of Ohio

[73] Assignee: The Standard Oil Company, Cleveland, Ohio

[21] Appl. No.: 135,206

[22] Filed: Dec. 21, 1987

[51] Int. Cl.$^5$ ............................................. C07F 9/90
[52] U.S. Cl. ........................................ 556/64; 556/76
[58] Field of Search ................................ 556/64, 76

[56] References Cited

PUBLICATIONS

Cotton and Wilkinson, "Advanced Inorganic Chemistry", 2nd. Ed., Interscience Publishers, N.Y. (1966), p. 517.
Lemerle et al., Journal de Chimie Physique, 71, pp. 97–100 (1974).
Jolivet et al., Bulletin de la Societe Chimique de France, No. 1-2, 27—33, (1977).

Primary Examiner—Paul F. Shaver
Attorney, Agent, or Firm—C. S. Lynch; D. J. Untener; L. W. Evans

[57] ABSTRACT

Disclosed is a method of making a tri- or tetrahydrocarbylammonium hexahydroxyantimonate,

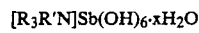 (1)

containing 3 to 30 C atoms, which process comprises the steps of (1) contacting a compound selected from

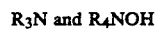

with the H$^+$ form of a solid cation exchange resin, and allowing the amine or the tetrahydrocarbylammonium hydroxide to react with the cation exchange resin, and thereafter (2) contacting the reacted resin with an aqueous solution of KSb(OH)$_6$,
wherein each R contains 1–10 C atoms and is independently selected from alkyl, aralkyl and alkylaralkyl, R' is H or H, and wherein x is an indeterminate number of moles of H$_2$O.

21 Claims, No Drawings

WATER-SOLUBLE ANTIMONY (V) COMPOUNDS

This invention relates to the preparation of new water-soluble salts of the hexahydroantimonate anion, and to such new compounds per se.

In the preparation of catalysts and other inorganic compositions containing antimony, conventional sources of antimony include the oxides $Sb_2O_3$ and $Sb_2O_4$. The oxides are poor sources of antimony due to their insolubility and concomitant low reactivity. Another common starting material is the alkali salt, $KSb(OH)_6$. This salt is moderately soluble in hot water, but is often not useful in catalyst preparation because of the poisoning effect of potassium in some catalysts, especially at the atom-for-atom level.

It is object of the invention to provide new water-soluble antimony (V) compounds.

It is another object of the invention to provide a novel process for making such compounds.

Other objects, as well as aspects, features and advantages, of the present invention will become apparent from a study of the accompanying disclosure and the claims.

These and other objects are realized as a result of the present invention according to one aspect of which there is provided a method of making a tri- or tetrahydrocarbylammonium hexahydroxyanimonate, $$[R_3R'N]Sb(OH)_6 \cdot xH_2O \quad (1)$$

containing 3 to 30 C atoms, which process comprises the steps of (1) contacting a compound selected from

with the $H^+$ form of a solid cation exchange resin, and allowing the amine or the tetrahydrocarbylammonium hydroxide to react with the cation exchange resin, and thereafter (2) contacting the reacted resin with an aqueous solution of $KSb(OH)_6$, wherein each R contains 1–10 C atoms and is independently selected from alkyl, aralkyl and alkylaralkyl, R' is H or R, and wherein x is an indeterminate number of moles of $H_2O$.

In the foregoing process, the total C atoms in the compound of formula (1) is usually from 3 to 24, more usually 3 to 18. In the antimonate products of formula (1) and in the reactants $R_3N$ and $R_4NOH$, it is most usual that 3 of the R groups are the same. It is also most usual that 3 of the R groups are alkyl, especially containing 1–6 C atoms, particularly 1–4 C atoms.

The new products of the invention of formula (1) are in most instances water soluble; even those compounds with the most C atoms that are not water soluble are water dispersible in the sense that they form emulsions in water because of their ionic nature.

Especially useful products of the invention are those in which 3 of the R groups are $C_1$ to $C_6$, particularly $C_1$ to $C_4$, alky groups, and R' contains 1–8 C atoms or is H.

In the process of the invention, when the reactant with the cation exchange resin in step (1) is an amine, the resin becomes charged with $R_3NH^+$ ions in step (1). When this reactant is $R_4NOH$ the cation exchange resin becomes charged with $R_4N^+$ ions and water results from the reaction of the $H^+$ ion of the resin with the $OH^-$ ion from the $R_4NOH$ reactant. Thereafter, when either charged form of the resin is contacted with the $KSb(OH)_6$ solution, the resin becomes charged with $K^+$ ions, and, of course, the product $[R_3HN]Sb(OH)_6$ or the product $R_4N]Sb(OH)_6$, respectively, results.

When compared to $KSb(OH)_6$, the highly dispersible products of the invention are much more easily incorporated in aqueous solutions and slurries of inorganic compounds in making inorganic compositions such as solid contact catalysts, ceramics and the like. Of equal importance is that 5-valent antimony can be introduced without the concomitant introduction of the potassium ion. Thus, the new counterions, i.e., the trihydrocarbylammonium or the tetrahydrocarbylammonium cation can be easily removed from the composition by oxidation or combustion at moderate calcination temperatures. Finally, the new antimonates of the present invention are easily dissolved in polar organic solvents because of the new counterions.

In the process of the invention, if it is desired that the new compound of formula (1) be substantially free of the $R_3N$ or $R_3R'NOH$ reactant, the product of step (1) can be washed with water to remove the occluded aqueous solution containing these starting materials before effecting step (2). For instance, the reacted cation exchange resin from step (1) can be placed in a column and then washed with pure water until the effluent from the column is essentially free of the amine or hydrocarbylammonium hydroxide, prior to carrying out step (2).

The following examples of the invention are exemplary and should not be taken as in any way limiting.

EXAMPLE 1

Tetra-n-butylammonium hexahydroxyantimonate was made as follows: A cation exchange resin (polystyrene crosslinked with 2% divinylbenzene, H form, 1.8 meq/ml wet capacity) was charged with $Bu_4N^+$ ions by stirring 330 ml resin (0.6 eq) with 55% aqueous tetra-n-butylammonium hydroxide solution (472 g, 1 eq) for 72 hours (an equal volume of deionized water was added for dilution purposes). The flask containing the stirred resin was sealed in order to prevent reaction of the strongly basic solution with atmospheric $CO_2$. A 250 ml portion of the charged resin was then transferred to a 300 ml column and washed with deionized water until the pH of the effluent matched the pH of deionized water. A solution of $KSb(OH)_6$ (20g) in 1 L of 60°–80° C. deionized water was prepared and cooled to near room temperature. This solution was passed through the resin column at a flow rate of about 1 ml per min. A total volume of 3.75 L of $KSb(OH)_6$ solution (0.275 eq) was passed through the column. The effluent was collected and subsequently rotovapped to dryness (bath temp <60° C.). A viscous oil was obtained. After drying in vacuo over $P_4O_{10}$ for 24 hr the oil was converted to an hygroscopic solid.

EXAMPLE 2

Trimethylammonium hexahydroantimonate was prepared as follows:

A cation exchange resin (polystyrene crosslinked with 2% divinylbenzene, $H^+$form, 1.8 meg/g wet capacity) was charged with $(H_3C)_3NH^+$ ions by stirring 300 ml resin (0.54 eq) with 170g (0.72 eq) of 25 wt% aqueous trimethylamine solution for 48 hours (200g of deionized water was added for dilution purposes). The flask containing the stirred resin was sealed in order to prevent reaction of the strongly basic solution with atmospheric $CO_2$. A 150 ml portion of the charged resin was then transferred to a 300 ml column and washed with deionized water until the pH of the effluent matched the pH of dionized water. A solution of $KSb(OH)_6$ (20 g) in 1 L of 60°–80° C. deionized water was prepared and cooled to near room temperature. This solution was passed through the resin column at a flow rate of about 1 ml per min. A total volume of 2.5L of $KSb(OH)_6$ solution was passed through the column. The effluent was collected and subsequently rotovapped to near dryness (bath temp < 60° C.).

EXAMPLE 3

Tetra-n-propylammonium hexahydroantimonate was prepared as follows:

A cation exchange resin (polystyrene crosslinked with 2% divinylbenzene, H form, 1.8 meq/ml wet capacity) was charged with tetra-n-propylammonium ions by stirring 330 ml resin (0.6 eq) with 40% aqueous tetra-n-propylammonium hydroxide solution (350 g) for 72 hours (an equal volume of deionized water was added for dilution purposes). The flask containing the stirred resin was sealed in order to prevent reaction of the strongly basic solution with atmospheric $CO_2$. A 250 ml portion of the charged resin was then transferred to a 300 ml column and washed with deionized water until the pH of the effluent matched the pH of deionized water. A solution of $KSb(OH)_6$ (20 g) in 1 L of 60°–80° C. deionized water was prepared and cooled to near room temperature. This solution was passed through the resin column at a flow rate of about 1 ml per min. A total volume of 3.75 L of $KSb(OH)_6$ solution (0.275 eq) was passed through the column. The effluent was collected and subsequently rotovapped to dryness (bath Temp. <60° C.). A viscous oil was obtained. After drying in vacuo over $P_4O_{10}$ for 24 hr the oil was converted to an hygroscopic solid.

EXAMPLE 4

Tetraethylammonium hexahydroantimonate was prepared as follows:

A cation exchange resin (polystyrene crosslinked with 2 % divinylbenzene, H form, 1.8 meq/ml wet capacity) was charged with tetraethylammonium ions by stirring 270 ml resin with 40% aqueous tetraethylammonium hydroxide solution (317.5 g) for 72 hours (an equal volume of deionized water was added for dilution purposes). The flask containing the stirred resin was sealed in order to prevent reaction of the strongly basic solution with atmospheric $CO_2$. A 250 ml portion of the resin was then transferred to a 300 ml column and washed with deionized water until the pH of the effluent matched the pH of deionized water. A solution of $KSb(OH)_6$ (20 g) in 1 L of 60°–80° C. deionized water was prepared and cooled to near room temperature. This solution was passed through the resin column at a flow rate of about 1 ml per min. A total volume of 3.75 L of $KSb(OH)_6$ solution (0.275 eq) was passed through the column. The effluent was collected and subsequently rotovapped to dryness (bath temp< 60° C.). A viscous oil was obtained. After drying in vacuo over $P_4O_{10}$ for 24 hr the oil was converted to an hygroscopic solid. The yield was essentially quantitative. The antimony content of a dried sample of the $[Et_4N]^+$ salt was determined by an iodometric titrimetic procedure. The average value of a number of titrations, 32.11% on a weight basis, corresponds to the formula $[(CH_3CH_2)_4N]Sb(OH)_6 \cdot 1.4H_2O$ (calculated 32.10%).

EXAMPLE 5

Tetramethylammonium hexahydroantimonate was prepared as follows:

A cation exchange resin (polystyrene crosslinked with 2% divinylbenzene, H form, 1.8 meq/ml wet capacity) was charged with tetramethylammonum ions by stirring 330 ml resin (0.6 eq) with 6.25% aqueous tetramethylammonium hydroxide solution (1600 g) for 72 hours (an equal volume of deionized water was added for dilution purposes). The flask containing the stirred resin was sealed in order to prevent reaction of the strongly basic solution with atmospheric $CO_2$. A 250 ml portion of the charged resin was then transferred to a 300 ml column and washed with deionized water until the pH of the effluent matched the pH of deionized water. A solution of $KSb(OH)_6$ (20 g) in 1 L of 60°–80° C. deionized water was prepared and cooled to near room temperature. This solution was passed through the resin column at a flow rate of about 1 ml per min. A total volume of 3.75 L of $KSb(OH)_6$ solution (0.275 eq) was passed through the column. The effluent was collected and subsequently rotovapped to dryness (bath temp <60° C.). A viscous oil was obtained. After drying in vacuo over $P_4O_{10}$ for 24 hr the oil was converted to an hygroscopic solid.

EXAMPLES 6, 7 and 8

When the procedure of Example 2 was repeated using triethyl-, tri-n-propyl and tri-n-butylamines, instead of trimethyl amine, there is obtained, respectively triethylammonium, tri-n-propylammonium and tri-n-butylammonium hexahydroantimonate.

As noted, the products of the present invention can be used to make catalyst compositions. An example is as follows:

EXAMPLE 9

9.47 g of $[Et_4N]Sb(OH)_6$, as in Example 4, were added to an aqueous solution of 2.02 g of $(VO)SO_4$ in 200 ml water, resulting in the immediate precipitation of a light blue solid. The suspension was brought to reflux to dissolve the precipitate. Excess ammonium acetate (2.0g) was then added in order to cause precipitation. The precipitate was isolated after centrifuging and pouring off the supernatant liquid. In a separate flask, 14.2 g of $[Et_4N]Sb(OH)_6$ were dissolved in water and excess ammonium acetate (11.7g) was added. This also resulted in the formation of a precipitate which was isolated by centrifugation. The two precipitates were then resuspended in 200 ml water which contained 2.31 g tungstic acid. The water was then removed by evaporative boiling and the resulting solid was supported on pre-gelled AlOOH SB by the following procedure: The catalyst precursor solids and 11.8g of AlOOH, equivalent to 10.0 g $A_2O_3$, were slurried in 40 ml of 10 percent acetic acid solution. This slurry was dried overnight at 110° C. and then heated 5 hours at 350° C., then crushed and screened to 20–35 mesh and, finally, calcined at 610° C. for 3 hours. Composition: $50\%VSb_5WO_x+50\%$ $Al_2O_3$.

This catalyst was used to ammoxidize propane over a fixed bed of the catalyst using molar feed ratios of 1 propane 2.0 $NH_3/3.0$ $O_2/6.7$ $N_2/3.0$ $H_2O$, using a reactor temperature of 500° C. and a contact time of 1.7 secs. Conversion of propane was 75%, and yields were 31% acrylonitrile, 7% propylene and 10% HCN.

As will be evident to those skilled in the art, various modifications of this invention can be made or followed in the light of the foregoing disclosure and discussion without departing from the spirit and scope of the disclosure or from the scope of the claims.

We claim:

1. A new compound, tri- or tetrahydrocarbylammonium hexahydroxyantimonate, having the formula $$[R_3R'N]Sb(OH)_6 \cdot xH_2O \qquad (1)$$

wherein each R contains 1–10 C atoms and is independently selected from alkyl, aralkyl and alkylaralkyl, R' is H or R, and wherein x is an indeterminate number of moles of $H_2O$.

2. A compound of claim 1 containing 3 to 24 C atoms.
3. A compound of claim 1 containing 3 to 18 C atoms.
4. A compound of claim 1 wherein 3 of the R groups are the same.
5. A compound of claim 1 wherein R' is is selected from alkyl, aralkyl and alkylaralkyl groups.
6. A compound of claim 4 wherein R' is R and 3 of the R groups are alkyl groups having 1–6 C atoms.
7. A compound of claim 6 wherein the fourth R group contains 1–8 C atoms and is selected from an alkyl, an aralkyl and an alkylaralkyl group.
8. A compound $$[R_3NH]Sb(OH)_6 \cdot xH_2O$$

according to claim 1 wherein each R group contains 1–4 C atoms.

9. Trimethylammonium hexahydroantimonate.
10. A compound of $$[R_4N]Sb(OH)_6 \cdot xH_2O$$

according to claim 1, wherein 3 of the 4 R groups contain 1–4 C atoms and the fourth R group contains 1–8 C atoms.

11. A compound of claim 1 wherein 3 of the 4 R groups are the same.
12. Tetra-n-butylammonium hexahydroantimonate.
13. Tetra-n-propylammonium hexahydroantimonate.
14. Tetraethylammonium hexahydroantimonate.
15. Tetramethylammonium hexahydroantimonate.
16. A compound which is a trihydrocarbylammonium hexahydroxyantimonate, having the formula $$[R_3HN]Sb(OH)_6 \cdot xH_2O \qquad (1)$$

wherein each R contains 1–10 C atoms and is independently selected from alkyl, aralkyl and alkylaralkyl, and wherein x is an indeterminate number of moles of $H_2O$.

17. A compound of claim 16 containing 3 to 24 C atoms.
18. A compound of claim 16 containing 3 to 18 C atoms.
19. A compound of claim 16 wherein the 3 R groups are the same.
20. A compound of claim 19 wherein each of the 3 R groups is an alkyl group having 1–6 C atoms.
21. A compound of claim 5, exclusive of tetramethylammonium hexahydroxyantimonate.

* * * * *

UNITED STATES PATENT AND TRADEMARK OFFICE
CERTIFICATE OF CORRECTION

PATENT NO. : 4,990,638

DATED : Feb. 5, 1991

INVENTOR(S) : Charles J. Besecker

It is certified that error appears in the above-identified patent and that said Letters Patent is hereby corrected as shown below:

In claim 11, delete "1" and insert therefor---10---.

Signed and Sealed this

Fourth Day of June, 1991

*Attest:*

HARRY F. MANBECK, JR.

*Attesting Officer*   *Commissioner of Patents and Trademarks*